United States Patent [19]

Garrison et al.

[11] Patent Number: 5,569,651
[45] Date of Patent: Oct. 29, 1996

[54] GENTLE ANTI-ACNE COMPOSITION

[75] Inventors: Mark S. Garrison, White Plains, N.Y.;
John A. Duffy, West Milford, N.J.;
Janice J. Teal, Old Greenwich, Conn.

[73] Assignee: Avon Products, Inc., Suffern, N.Y.

[21] Appl. No.: 397,784

[22] Filed: Mar. 3, 1995

[51] Int. Cl.[6] .................................................. A61K 7/48
[52] U.S. Cl. ........................ 514/159; 514/557; 514/844
[58] Field of Search .......................... 424/401; 514/844, 514/159, 557

[56] References Cited

U.S. PATENT DOCUMENTS 4,105,783  8/1978  Yu ............................................. 424/283
4,608,370  8/1986  Aronsohn .................................. 514/159
5,382,432  1/1995  McCook ................................... 424/401

*Primary Examiner*—C. Warren Ivy
*Assistant Examiner*—Evelyn Huang
*Attorney, Agent, or Firm*—Hopgood, Calimafde, Kalil & Judlowe

[57] ABSTRACT

A topical anti-acne treatment which comprises salicylic acid and lactic acid, adjusted to a selected pH and placed in a suitable vehicle, such disclosed formulations can be used by individuals with adult acne, rosacea and sensitive skin complicated with acne.

1 Claim, No Drawings

GENTLE ANTI-ACNE COMPOSITION

FIELD OF INVENTION

The present invention relates to compositions for topical anti-acne treatment. More particularly, the invention comprises salicylic acid and lactic acid adjusted to a selected pH and combined with a suitable vehicle for treating adult acne and sensitive skin conditions such as rosacea complicated with acne.

BACKGROUND OF THE RELATED ART

Traditional acne medications are principally formulated for the teenage market, i.e., products designed for young, oily skin. Teenagers undergoing hormonal changes have skin conditions which are prone to acne break out which is aggravated by oily, sebaceous gland secretions. Current therapies for common acne or "teen acne" are designed to dry oily skin, frequently with harsh solvents such as volatile alcohols. While this may be appropriate for teenage applications, adults and those with sensitive skin conditions such as rosacea find conventional products intolerable. This intolerance manifests itself as a stinging or burning sensation upon application and usually worsens the acne condition being treated.

"Adult acne" has multiple etiologies and mechanisms of pathogenesis which are different from common or teen acne. The major clinical differences include distinctive hormonal patterns which cause changes in the location and type of lesions. In common acne, lesions appear in the perinasal and forehead regions of teenagers, whereas the adult condition usually forms lesions on the chin and neck immediately beneath the mandibles. In teen acne the typical lesion is a comedone otherwise known as a "pimple." Adults tend to form lesions which are primarily inflammatory.

Adult and teen women have different androgen levels which contribute to a variation in oil secretion from the respective skin types. The differences in androgen levels are readily detected by measuring serum content for free dehydro-epiandrosterone sulfate (DHEA-S), luteinizing hormone (LH) and follicle stimulating hormone (FSH). Adult women with acne have relatively elevated androgen levels when compared to female teenagers.

Rosacea is a fairly common dermal condition characterized by sensitive skin which is easily irritated. Starting in the mid to late twenties, increasing telangiectasia (spider veins), inflammatory papules, pustules and nodules develop. In the worst forms, granulomatous inflammatory lesions may result, along with the progressive thickening and coarseness of skin. Rosacea complicated with acne is difficult to treat because of the tendency for hypersensitivity and side effects in this group, particularly when known alcoholic solutions, lotions and gels are applied to an individual's skin.

Irritant folliculitis, caused by epithelial irritations, is another sensitive skin condition which manifests as erythematous papules and follicular pustules. Recurrent episodes of irritant folliculitis are sometimes misdiagnosed as common acne and treated with physical abrasives and exfoliants which traumatize and aggravate the original condition.

The use of salicylic acid in the treatment of common or teen acne is known. For example, U.S. Pat. No. 4,665,063 describes the use of topically applied aspirin (acetyl salicylic acid) for treating common acne; and U.S. Pat. No. 4,891,227 describes the use of pads for applying anti-acne products containing salicylic acid for oily skin. These patents describe state-of-art compositions which emphasize aggressive chemical and physical treatment suitable for teen acne, without addressing the suitability for adult acne and/or the need for mildness.

U.S. Pat. No. 4,800,197 describes a combination of salicylic acid and an anionic taurate surfactant, specifically sodium methyl cocoyl taurate or sodium methyl oleoyl taurate. U.S. Pat. No. 5,296,476 describes the specific use of salicylic acid in combination with calcium citrate. Again, these treatment modalities are designed for aggressive, physical cleansing, which assumes that the individual indicators are normal, young and oily skin.

Currently available forms of salicylic acid tend to aggravate the relatively dry adult acne, and they are particularly unsuitable for those with sensitive skin conditions such as irritant folliculitis. Known salicylic acid preparations are also poorly tolerated in patients suffering from acne complexed with rosacea.

The art also teaches the use of lactic acid for teenage problem skin. See, for example, U.S. Pat. Nos. 3,879,537, 4,234,599, 4,363,815 and 4,380,549 which generally describe the use of alpha-hydroxy acids such as lactic and citric acids for titrating pH in antibiotic preparations. These antibiotic therapies assume that teen acne has predominant etiological ties to opportunistic bacterial infections like those found in acne vulgaris. U.S. Pat. No. 4,507,319 describes the use of lactic acid for adjusting pH in a composition comprising derivatives of 2-hydroxy-octanoic acid or 2-keto-octanoic acid; and U.S. Pat. No. 4,330,531 describes a germ killing composition containing lactic acid which produces chlorine dioxide gas for antibacterial effects on acne vulgaris.

The use of lactic acid derivatives is also known. U.S. Pat. No. 3,806,593 discloses the use of esters of lactic acid; and U.S. Pat. No. 4,540,567 describes the use of lactate esters, preferably ethyl lactate. U.S. Pat. Nos. 4,613,592 and 4,772,592 also refer to lactate esters in compositions which have silicone oil and a $C_1$–$C_4$ alkanol.

Separate uses of salicylic acid and lactic acid in preparations for treating common acne are well known to the relevant art. But, until the present invention, a lactic acid-salicylic acid combination for treating acne of any kind had not been recognized. More significantly, there was no recognition of a lactic acid-salicylic acid combination which is mild and suitable for adult acne and/or sensitive skin compounded with acne.

In fact, the use of lactic acid as an acne medication is discouraged by prior art assays which clinically evaluate sensitive skin by measuring an individual's intolerance to dilute lactic acid solutions. P. Frosch and A. Kligman, *A Method for Appraising the Stinging Capacity of Topically Applied Substances*, J. Soc. Cosmet. Chem., Vol. 28, pages 197–209 (May 1977).

Based on these considerations, there is a need in the art for a therapeutic dermal composition which is well tolerated by individuals with adult acne and other sensitive skin conditions complicated with acne. To this end, the present invention contemplates at least the following goals.

OBJECTS OF THE INVENTION

It is an object of the present invention to provide a mild salicylic acid composition for topical treatment of adult acne and acne-complicated sensitive skin.

Another object of the present invention is to provide a composition comprising salicylic acid and lactic acid, adjusted to a selected pH and placed in a suitable vehicle to provide a gentle topical formulation which is appropriate for use by those with adult acne and other sensitive skin conditions such as rosacea compounded by acne.

A further object of the present invention is to provide a composition containing a selected range of lactic acid which has a synergistic effect with a selected range of salicylic acid for raising the tolerance levels of sensitive skin to both ingredients, while providing the therapeutic benefits of the two ingredients.

These and other objects will become evident from the disclosure provided below.

SUMMARY OF INVENTION

The present invention is directed to a mild, topical formulation for treating adult acne and sensitive skin conditions complicated with acne, which comprises about 0.05 to about 5.0% salicylic acid; about 0.5 to about 15.0% lactic acid; sufficient pH adjustor to maintain pH in the range of about 3.8 to about 4.5; and a vehicle which maintains the active ingredient levels, desired pH and mildness.

The formulation can be prepared in several different vehicles. For example, a lotion embodiment may have about 6.5% propylene glycol dicaprylate/dicaprate; about 6.0% lactic acid; about 5.0% glycerin; about 3.0% ammonium hydroxide; about 2.0% Peg 40 Stearate; about 1.5% Steareth-2; about 0.6% hydroxyethyl cellulose; about 0.6% xanthan gum; about 0.5% salicylic acid; about 0.2% methylparaben; about 0.2% disodium EDTA; about 0.2% vitamin-E acetate and about 0.3% natural extracts from apple, grape, mango, orange and geranium.

DETAILED DESCRIPTION OF THE INVENTION

One inventive composition includes salicylic acid and lactic acid adjusted to selected pH ranges and mixed in a suitable vehicle such as lotions, creams, gels or other carriers which maintain the active ingredient levels, desired pH and inherent mildness. The general and preferred ranges in the following examples are expressed as weight percents.

EXAMPLE 1

Lotion Embodiment

|  | General | Preferred |
| --- | --- | --- |
| Salicylic Acid | 0.05–5.0% | 0.5–2.0% |
| Lactic Acid | 0.5–15.0% | 5.0–10.0% |
| Glycerin | 0.1–10.0% | 0.5–6.0% |
| Propylene Glycol Dicaprylate/Dicaprate | 0.5–10.0% | 2.0–8.0% |
| Peg 40 Stearate | 0.5–5.0% | 1.8–4.0% |
| Steareth-2 | 0.2–3.0% | 1.0–2.5% |
| Xanthan Gum | 0.1–1.0% | 0.25–0.7% |
| Hydroxyethyl Cellulose | 0.1–1.0% | 0.25–0.7% |
| Disodium EDTA | 0.05–0.25% | 0.15–0.20% |
| Methylparaben | 0.1–0.3% | 0.20–0.25% |
| Ammonium Hydroxide 30% aqueous qs to pH | pH 3.8–4.5 | pH 4.15–4.25 |
| Water | qs to 100% | |

In the lotion embodiment illustrated above, glycerin acts as a humectant and moisturizer; propylene glycol dicaprylate/dicaprate is used as an emollient/moisturizer; Peg-40 stearate and Steareth-2 act as the primary and secondary emulsifiers, respectively; xanthan gum and hydroxyethyl cellulose are used for thickening; disodium EDTA acts as a chelator to sequester any discoloration causing metal ions; and methylparaben is used as a preservative. Ammonium hydroxide is used to partially neutralize the lactic and salicylic acids and raise the pH to its required levels. Other suitable pH adjustors include sodium hydroxide, potassium hydroxide and triethanolamine.

EXAMPLE 2

Cream Embodiment

|  | General | Preferred |
| --- | --- | --- |
| Salicylic Acid | 0.05–5.0% | 0.5–2.0% |
| Lactic Acid | 0.5–15.0% | 5.0–10.0% |
| Glycerin | 0.1–5.0% | 0.5–4.0% |
| Propylene Glycol Dicaprylate/Dicaprate | 0.5–8.0% | 2.0–6.0% |
| Steareth-20 | 0.5–4.0% | 1.8–3.0% |
| Steareth-2 | 0.2–2.5% | 0.8–2.0% |
| Xanthan Gum | 0.1–1.0% | 0.25–0.6% |
| Hydroxyethyl Cellulose | 0.1–1.0% | 0.25–0.6% |
| Cetyl Alcohol | 0.3–3.0% | 1.0–2.5% |
| Glyceryl Monostearate | 0.5–4.9% | 0.9–3.5% |
| Disodium EDTA | 0.05–0.25% | 0.15–0.20% |
| Imidazolidinyl Urea | 0.1–0.5% | 0.2–0.3% |
| Vitamin E Acetate | 0.05–0.2% | 0.1–0.2% |
| Ammonium Hydroxide 30% aqueous qs to pH | pH 3.8–4.5 | pH 4.15–4.25 |
| Water | qs to 100% | |

In the cream embodiment illustrated above, glycerin, propylene glycol dicaprylate/dicaprate, disodium EDTA and ammonium hydroxide perform similar functions described for the lotion embodiment. Steareth-20 and Steareth-2 act as the primary and secondary emulsifiers, respectively; cetyl alcohol, glyceryl monostearate, xanthan gum and hydroxyethyl cellulose are all used for thickening; and imidazolidinyl urea is used as a preservative.

EXAMPLE 3

Gel Embodiment

|  | General | Preferred |
| --- | --- | --- |
| Salicylic Acid | 0.05–4.0% | 0.5–2.0% |
| Lactic Acid | 0.5–12.0% | 4.0–9.0% |
| Disodium EDTA | 0.05–0.25% | 0.15–0.20% |
| Propylene Glycol | 0.5–9.0% | 2.0–6.0% |
| Hydroxyethyl Cellulose | 0.3–2.0% | 0.4–1.5% |
| Botanical Extracts | 0.1–2.0% | 0.2–1.5% |
| Methylparaben | 0.1–0.3% | 0.20–0.25% |
| Ammonium Hydroxide 30% aqueous qs to pH | pH 3.8–4.5 | pH 4.15–4.25 |
| Water | qs to 100% | |

In the gel embodiment illustrated above, disodium EDTA, hydroxyethyl cellulose, methylparaben and ammonium hydroxide perform the same or similar functions disclosed for the lotion and cream embodiments. Propylene glycol acts as a humectant and botanical extracts (such as chamomile extract) contributes to gentleness.

The preceding examples serve only to illustrate, but not limit, the present invention. Each embodiment was made according to the general protocol outlined below. One skilled in the art could easily apply the disclosure provided in this specification to develop further embodiments and other suitable vehicles without departing from the scope of this invention.

EXAMPLE 4

Preparation of Formulas

To prepare the invention, a quantity of water was mixed in a first tank with disodium EDTA, lactic acid, salicylic acid and sufficient ammonium hydroxide to achieve a pH between 4.15 and 4.25. This mixing was initiated at room temperature, but the batch temperature rose about 10° F. due to the exothermic nature of the neutralization reaction. The batch was slowly sweep-mixed for about 15 minutes, then heated to a range of about 175°–180° F.

Glycerin was next added (for lotion and cream embodiments) and mixed continuously for 10–15 minutes. Hydroxyethylcellulose and other thickeners were then slowly sprinkled into the mixture and the sweep was disengaged. The resulting batch was milled (an equivalent vigorous high shear type of mixing is equally effective) for about one hour until a uniform consistency was achieved. Sweep mixing was then resumed and any entrapped air was allowed to rise in this first phase. The temperature was maintained in the first tank at about 160°–165° F.

In a second tank, the oil phase plus emulsifiers were heated at 170°–175° F. and mixed to a uniform consistency. For the lotion, the ingredients in this step were propylene glycol dicaprylate/dicaprate, methylparaben, Steareth-2 and Peg 40 stearate; in the cream, the ingredients comprised propylene glycol dicaprylate/dicaprate, Steareth-20 and Steareth-2; and in the gel, the ingredients included propylene glycol and methylparaben. The resulting mixture (in the second tank) was put through a 200 micron strainer and subsequently added to the first tank containing the first phase.

The first phase (in the first tank) was continuously milled during transfer and the resulting batch was further milled for about five minutes after the transfer operation was complete. Following milling, the batch was sweep-mixed slowly for about 10 minutes and allowed to cool to 90°–95° F. Slow mixing was continued and other ingredients such as vitamins, botanicals, additional emollients and oils, to suit the particular target product variations, were added. Fragrances were next added. One skilled in the art will easily note that additional ingredients can be introduced in this concluding step or earlier to create other variations which are covered by the scope of this disclosure.

Samples from the top and bottom of the final batch were taken to the quality assurance lab and checked to confirm that pH, viscosity, specific gravity, color, odor and product texture were within specifications. If pH needs further adjustment, the batch can be fine tuned for the desired pH range. Finally, the presence of preservative was confirmed and the level of salicylic acid was checked analytically for required concentration levels.

EXAMPLE 5

Usage Survey

The formulations of the present invention are highly effective in the treatment of adult acne and rosacea/sensitive skin complicated with acne, without causing cutaneous irritations. This example summarizes the results of an acceptance study using the lotion embodiment illustrated above. All test participants were female, aged 30–35. None of the participants had oily skin, but 59% exhibited adult acne or acne aggravated sensitive skin and approximately 33% showed some characteristics of acne rosacea.

The objectives included an assessment, under blind conditions, of the overall aesthetics, acceptability and perceived performance of this product among the above-noted sample representing a target female population to determine if these women perceive the product to perform in line with their expectations.

The study design included an eight week facial use test, with periodic telephone callback interviews. This quantitative study was fielded in five geographically dispersed locations, for a total of 200 women, with 40 per location. All raw data was processed through statistical analysis using the SAS statistical package.

The results indicate that the majority of respondents rated the product favorably and were pleased with the aesthetics of the lotion. Improvements to their skin were in line with the respondents' objective and subjective expectations. Very importantly, these improvements occurred in the absence of any signs of irritation despite the sensitive skinned nature of significant portions of the panel.

In sum the formulation is highly effective in the treatment of adult acne and rosacea/sensitive skin complicated with acne, without the occurrence of undesirable irritation.

EXAMPLE 6

Clinical Trials

Extended clinical trials were also conducted to evaluate the efficacy of the lotion embodiment. The subjects of this study were selected based on frequent occurrences of adult acne and/or sensitive skin complexed with acne. Consistent with Example 5, particular emphasis was placed on treating acne conditions without drying and irritating the skin.

The study was a baseline controlled six month test, with evaluations of facial skin occurring at 4, 9, 12, 18 and 24 weeks. The product's effectiveness was principally evaluated by clinical grades from attending dermatologists. Panelists returned to the study site every two weeks for a compliance check.

The universe was originally separated into two (2) subpopulations—Group A with adult acne and Group B with acne rosacea. This was done to assess the present invention's potential to create adverse reactions in those with sensitive skin (i.e., the rosacea group). After four weeks, there was no indication of tolerance problems or reactions to the product. The groups were subsequently combined for data analysis purposes.

Forty-one (41) women ranging in age from 28 to 49 (with an average age of 38.0±5.3) completed the 24 week program. Participants were selected according to the Fitzpatrick scale, Skin Types I, II or III. A recent history of acne breakout or similar skin disorders was also required. Each participant was examined by a physician to confirm the existence of one or more of the following conditions.

1. Follicular papules—small pin-point sized raised bumps associated with irritation of the follicles
2. Papules—relatively large red inflammatory lesions
3. Pustules—raised, pus filled inflammatory bumps
4. Blackheads—a specific type of clogged pore which is covered with a black "cap" and is slightly raised above the skin surface In addition, rosacea attributes were recorded by noting diffuse redness and general erythema of the skin caused by permanently dilated capillaries or telangiectasia.

The test product was a white lotion with a light citrus scent. It contained 0.5% salicylic acid and 6.0% lactic acid, with a pH between 4.2 and 4.4. The lotion was supplied in four 1 ounce glass bottles. For the first two weeks, test participants were instructed to apply the lotion once a day, preferably at night after cleansing the face. After two weeks, the lotion was applied in the morning and evening until symptoms were diminished.

Test results were collected in response to written and oral questions. Statistical analysis of the raw data was performed by a consulting statistician. Incomplete data was excluded from the analysis and conventional methods were used to verify statistical significance.

Most parameters exhibited significant improvement during the first four weeks. The following table indicates the point of first significant improvement for each parameter; the percentage of panelists who improved at intermediate points; and the percentage of panelists who improved when the program was complete.

| Parameter | First Improvement | Percent Improvement | Percent Improvement (24 Weeks) |
|---|---|---|---|
| Follicular Papules | 4 Weeks | 94% | 97% |
| Papules | 4 Weeks | 94% | 97% |
| Clogged Pores | 4 Weeks | 79% | 97% |
| Overall Rosacea | 4 Weeks | 76% | 86% |
| Blackheads | 4 Weeks | 57% | 86% |
| Diffuse Redness | 9 Weeks | 48% | 80% |
| Pustules | 12 Weeks | 100% | 100% |

The product was well tolerated by the study population (including those with sensitive skin) and the attending dermatologist did not observe any adverse reactions during the study. Dramatic improvements were noted in the rosacea subgroup with markedly diminished acne and a lessening of the ruddy complexion associated with that condition. This clinical study demonstrates that the present formulations effectively treat sensitive skin acne and reduce adult acne breakouts.

Various modifications and alterations to the present invention may be appreciated based on a review of this disclosure. These changes and additions are intended to be within the scope and spirit of this invention as defined by the following claims.

What is claimed is:

1. A topical formulation for treating adult acne and sensitive skin conditions complicated with acne, which consists of:

(a) about 6.5% propylene glycol dicaprylate/dicaprate;
   (b) about 6.0% lactic acid;
   (c) about 5.0% glycerin;
   (d) about 3.0% ammonium hydroxide;
   (e) about 2.0% Peg 40 Stearate;
   (f) about 1.5% Steareth-2;
   (g) about 0.6% hydroxyethyl cellulose;
   (h) about 0.6% xantham gum;
   (i) about 0.5% salicylic acid;
   (j) about 0.2% methylparaben;
   (k) about 0.2% disodium EDTA: and
   q.s. water.

* * * * *